(12) United States Patent
Mackool

(10) Patent No.: US 10,568,734 B2
(45) Date of Patent: Feb. 25, 2020

(54) ADJUSTING THE APODIZATION PATTERN FOR DIFFRACTIVE IOLS

(71) Applicant: NOVARTIS AG, Basel (CH)

(72) Inventor: Richard J. Mackool, Astoria, NY (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/059,581

(22) Filed: Mar. 3, 2016

(65) Prior Publication Data
US 2017/0252151 A1    Sep. 7, 2017

(51) Int. Cl.
A61F 2/16 (2006.01)
G02C 7/02 (2006.01)
G02B 5/18 (2006.01)

(52) U.S. Cl.
CPC .......... *A61F 2/1654* (2013.01); *A61F 2/1618* (2013.01); *G02B 5/1895* (2013.01); *G02C 7/024* (2013.01); *A61F 2002/1683* (2013.01)

(58) Field of Classification Search
CPC ..... A61F 2/1654; A61F 2/1656; G02C 7/027; G02C 7/041; G02C 7/042; G02C 2202/20
See application file for complete search history.

(56) References Cited

U.S. PATENT DOCUMENTS

| | | | | |
|---|---|---|---|---|
| 5,054,905 A | * | 10/1991 | Cohen | G02B 5/1876 351/159.42 |
| 5,056,908 A | * | 10/1991 | Cohen | G02B 5/1876 351/159.44 |
| 5,699,142 A | * | 12/1997 | Lee | A61F 2/1618 351/159.11 |
| 7,572,007 B2 | * | 8/2009 | Simpson | A61F 2/1654 351/159.44 |
| 8,500,805 B2 | * | 8/2013 | Kobayashi | A61F 2/1618 351/159.11 |
| 2006/0098163 A1 | * | 5/2006 | Bandhauer | A61F 2/1613 351/159.41 |

(Continued)

FOREIGN PATENT DOCUMENTS

| | | |
|---|---|---|
| CN | 101868197 A | 10/2010 |
| CN | 104918580 A | 9/2015 |
| CN | 105093585 A | 11/2015 |

OTHER PUBLICATIONS

China National Intellectual Property Administration, Chinese First Office Action, Application No. 201780012878.9, dated Aug. 22, 2019, 18 pages.

*Primary Examiner* — Paul B Prebilic
(74) *Attorney, Agent, or Firm* — Baker Botts L.L.P.

(57) ABSTRACT

An ophthalmic device including an ophthalmic lens having anterior and posterior surfaces and at least one diffraction grating is described. The diffraction grating(s) are on the anterior and/or posterior surface(s). The diffraction grating(s) include zones. A first zone is at a first distance range from a center of the lens. A second zone is at a second distance range further from the center than the first distance range. A repeat zone is at a third distance range further from the center than the second distance range. The first zone includes echelette(s) having a first step height and a first radius of curvature. The second zone includes echelette(s) having a second step height and a second radius of curvature. The repeat zone includes echelette(s) having at least one of the first step height and the first radius of curvature.

5 Claims, 4 Drawing Sheets

(56) References Cited

U.S. PATENT DOCUMENTS

| | | | |
|---|---|---|---|
| 2008/0300679 A1* | 12/2008 | Altmann | A61F 2/1654 623/6.31 |
| 2009/0323020 A1 | 12/2009 | Zhao et al. | |
| 2010/0312337 A1* | 12/2010 | Zhang | A61F 2/1613 623/6.31 |
| 2011/0292335 A1* | 12/2011 | Schwiegerling | A61F 2/1613 351/159.44 |
| 2012/0224138 A1* | 9/2012 | Cohen | A61F 2/1656 351/159.11 |
| 2013/0090730 A1* | 4/2013 | Weeber | A61F 2/1618 623/6.3 |
| 2013/0201445 A1* | 8/2013 | Das | A61F 2/1654 351/159.44 |
| 2013/0278891 A1* | 10/2013 | Zhao | A61F 2/1618 351/159.44 |
| 2014/0172088 A1* | 6/2014 | Carson | A61F 2/1656 623/6.3 |
| 2018/0092739 A1* | 4/2018 | Pagnoulle | A61F 2/1618 |

* cited by examiner

ADJUSTING THE APODIZATION PATTERN FOR DIFFRACTIVE IOLS

BACKGROUND

Intraocular lenses (IOLs) are implanted in patients' eyes either to replace a patient's lens or, in the case of a phakic IOL, to complement the patient's lens. Some conventional IOLs are single focal length IOLs, while others are multifocal IOLs. Single focal length IOLs have a single focal length or single power. Objects at the focal length from the eye/IOL are in focus, while objects nearer or further away may be out of focus. Multifocal IOLs, on the other hand, have at least two focal lengths. For example, a bifocal IOL has two focal lengths for improving focus in two ranges: a far region corresponding to a longer focal length and a near region corresponding to a shorter focal length. A trifocal IOL has three focal lengths corresponding to a near region, an intermediate region and a far region. Other multifocal lenses may have another number of focal lengths To provide multiple focal lengths, multifocal IOLs typically divide the lens into zones (e.g. annular regions) based upon the distance from the center of the lens. One or more zones near the center of the lens are configured for near vision. The zones farther from the center of the lens are configured for far vision. For example, some conventional IOLs may utilize diffraction to provide multiple focal lengths. Diffractive IOLs utilize a diffraction grating formed on a base curve on the surface of the IOL. The base curve corresponds to the radius of curvature for the lens. The diffraction grating typically takes the form of microscopic echelettes, or surface saw-tooth like facets, formed on the lens surface. The echelettes form a diffraction grating having a particular focal length. Each zone includes a set of echelettes having a particular step height and radius of curvature. Zone(s) closer to the center of the lens may have echelettes configured for a shorter focal length and may be dedicated to near vision. Zones closer to the edge of the lens may have echelettes configured for a longer focal length and may be dedicated to far vision.

In addition, the zones may also be apodized to reduce artifacts such as glare or halos. Apodization decreases the step heights of the echelettes with increasing distance from the center of the lens. In addition to zones further from the center being dedicated to far vision, therefore, the step heights of the echelettes for these zones are shorter.

Although the conventional diffractive IOLs function acceptably well in most patients, further improvements are desired. For example, patients may not only require different corrective powers, but the physical characteristics of the patients' eyes may also differ. For example, patients having eye geometries that vary from the norm may have limited success with a particular IOL. Accordingly, what is needed is a system and method for improving the performance of IOLs for a variety of patients.

BRIEF SUMMARY

A method and system provide an ophthalmic device. The ophthalmic device includes an ophthalmic lens having an anterior surface, a posterior surface and at least one diffraction grating. The diffraction grating(s) are disposed on at least one of the anterior surface and the posterior surface. The diffraction grating(s) include zones corresponding to distance ranges from a center of the anterior and/or posterior surface. The zones include a first zone corresponding to a first distance range, a second zone corresponding to a second distance range further from the center than the first distance range and a repeat zone corresponding to a third distance range further from the center than the second distance range. The first zone includes echelette(s) having a first step height and a first radius of curvature. The second zone includes echelette(s) having a second step height and a second radius of curvature. The repeat zone includes echelette(s) having at least one of the first step height and the first radius of curvature.

DETAILED DESCRIPTION OF THE PREFERRED EMBODIMENTS

The exemplary embodiments relate to IOLs including diffractive gratings. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system provide an ophthalmic device. The ophthalmic device includes an ophthalmic lens having an anterior surface, a posterior surface and at least one diffraction grating. The diffraction grating(s) are disposed on at least one of the anterior surface and the posterior surface. The diffraction grating(s) include zones corresponding to distance ranges from a center of the anterior and/or posterior surface. The zones include a first zone corresponding to a first distance range, a second zone corresponding to a second distance range further from the center than the first distance range and a repeat zone corresponding to a third distance range further from the center than the second distance range. The first zone includes echelette(s) having a first step height and a first radius of curvature. The second zone includes echelette(s) having a second step height and a second radius of curvature. The repeat zone includes echelette(s) having at least one of the first step height and the first radius of curvature.

Figure 1:
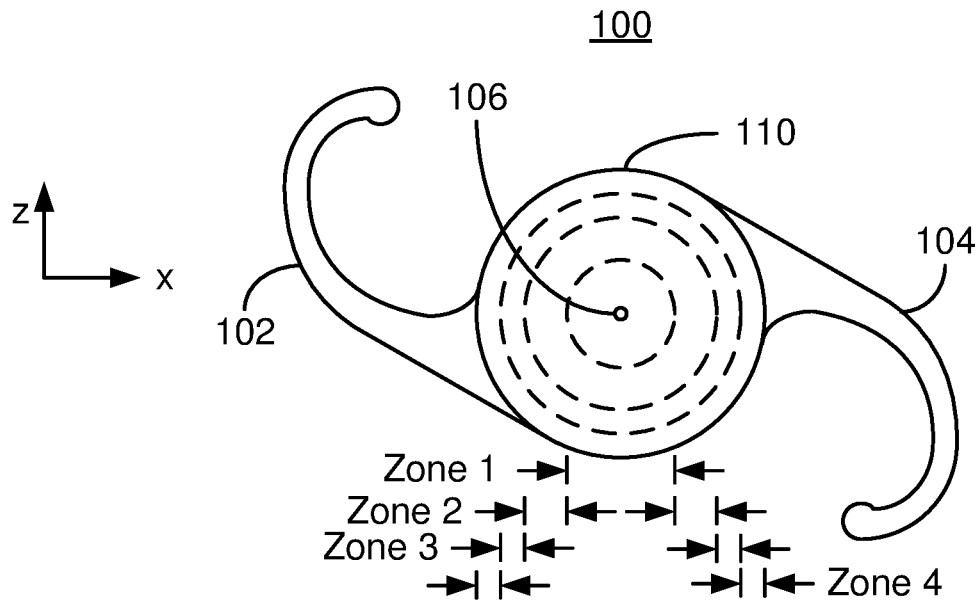
FIG. 1 depicts a plan view of an exemplary embodiment of an ophthalmic device.
Figure 2:
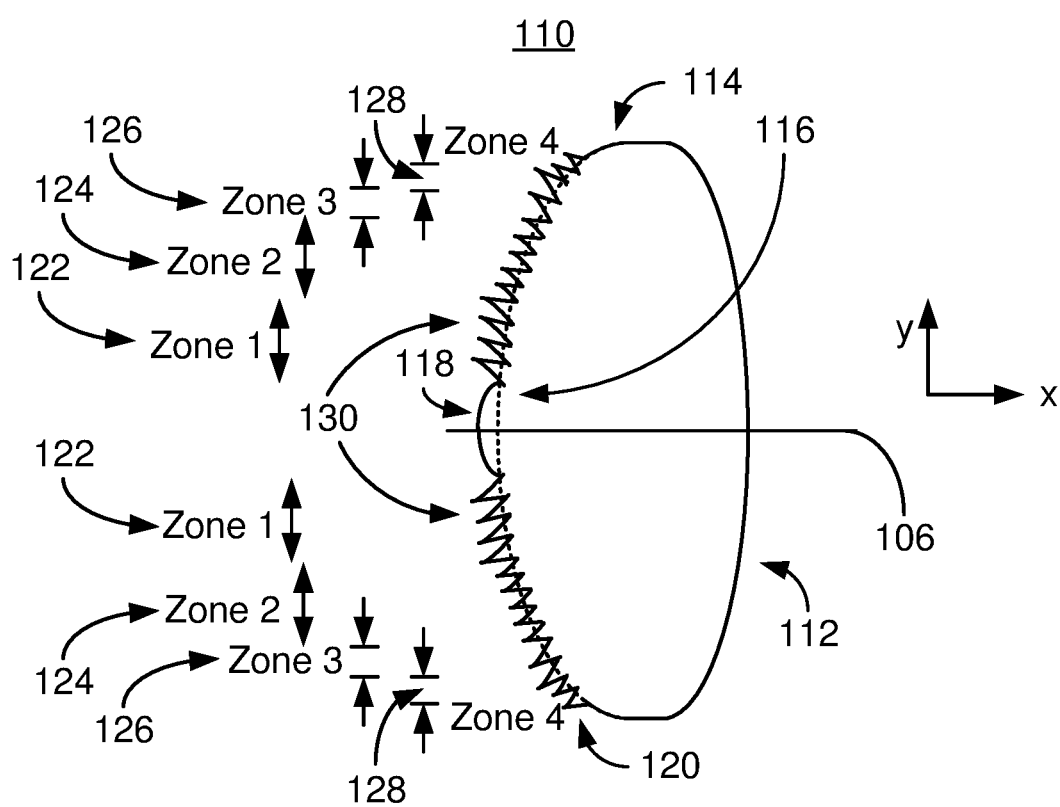
FIG. 2 depicts a side view of an exemplary embodiment of a lens of an ophthalmic device.

FIGS. 1-2 depict an exemplary embodiment of an ophthalmic device 100 that may be used as an IOL. FIG. 1 depicts a plan view of the ophthalmic device 100, while FIG. 2 depicts a side view of the ophthalmic lens 110. For clarity, FIGS. 1 and 2 are not to scale. The ophthalmic device 100 includes an ophthalmic lens 110 as well as haptics 102 and 104. The ophthalmic lens may be made of a variety of optical materials including but not limited to one or more of silicone, a hydrogel and an acrylic. Haptics 102 and 104 are used to hold the ophthalmic device 100 in place in a patient's eye (not explicitly shown). However, in other embodiments, other mechanism(s) might be used to retain the ophthalmic device in position in the eye. For clarity, the haptics are not depicted in FIGS. 2-7, discussed below. Although the ophthalmic lens 110 is depicted as having a circular cross section in the plan view of FIG. 1, in other embodiments, other shapes may be used.

The ophthalmic lens 110 (hereinafter "lens") has an optic axis 106 as well as posterior surface 112 and anterior surface 114. Although termed part of the lens 110, the optic axis 106 may be considered an imaginary line that passes through the centers of the anterior surface 114 and posterior surface 112. The optic axis 106 may also be perpendicular to the surfaces 112 and 114 at the point at which it passes through the surfaces 112 and 114.

The anterior surface 114 and posterior surface are characterized by a base curve. The base curve describes the curvature of the surface in the absence of other features such as diffraction gratings. In the embodiment shown, a diffraction grating 120 is formed into the anterior surface 114, while no such grating is present on the posterior surface 112. Thus, the base curve for the posterior surface 112 is the surface 112 itself. Because the anterior surface 114 includes a diffraction grating 120, the base curve 116 for the anterior surface 114 is shown by the dotted line in FIG. 2.

The anterior surface 114 includes a diffraction grating 120 formed of echelettes 130. In alternate embodiments, an additional diffraction grating (not shown) may be provided on the posterior surface 112. In such embodiments, the lens 110 has gratings on both surfaces 112 and 114. In still other embodiments, the diffraction grating 120 may reside on the posterior surface 112 instead of the anterior surface 114. The echelettes 130 are steps, typically microscopic in size, that form the diffraction grating 120. Each echelette 130 is characterized by a step height (hereinafter "height") and a radius of curvature. The height is the difference between the top of the echelette and the bottom of the echelette. The radius of curvature can be seen as the curvature of the echelette. The radius of curvature can also be seen as the difference between the base curvature and the curvature of the side of the echelette 130. For simplicity, only two echelettes 130 are labeled.

The lens 110, and thus the anterior surface 114 and diffraction grating 120, is divided into zones having different radial distances from the optic axis 106. In the embodiment shown, the ophthalmic lens 110 is divided into four zones: Zone 1 122, Zone 2 124, Zone 3 126 and Zone 4 128. Each zone 122, 124, 126 and 128 is annular. At the center of the anterior surface 114 is refractive element 118. In other embodiments, the refractive element 118 may be omitted. In such an embodiment, Zone 1 122 is a circle corresponding to a zero radius (the optic axis) up to a first, smallest radius. In the embodiment shown, however, Zone 1 122 is an annular ring from a first minimum radius to a second radius. Zone 2 124 is an annular ring from the second radius to a third radius that is larger than the second radius. Zone 3 126 is an annular ring from the third radius to a fourth radius that is larger than the third radius. Zone 4 128 is an annular ring from the fourth radius to a fifth radius that is larger than the fourth radius. Thus, the zones 122, 124, 126 and 128 correspond to four distance ranges. In the embodiment shown, Zone 4 128 extends almost to the outer edge of the lens 110. However, in other embodiments, the zones need not extend as close to the outer edge of the lens 110. In still other embodiments, the zones may extend to the outer edge of the lens 110. Four zones are shown for illustrative purposes only. In other embodiments, another number of zones may be included. For example, as few as three zones or greater than four zones may be present. In general, the lens 110 may have a larger number of zones. The width and position of the zones 122, 124, 126 and 128 may depend upon factors such as the desired focal lengths of the zones 122, 124, 126 and 128.

The echelettes 130 of the diffraction grating 120 differ in the zones 122, 124, 126 and 128. More specifically, the radii of curvature of the surfaces of the echelettes 130, the heights of the echelettes 130 and/or the distance between echelettes 130 (i.e. the period of the grating 120) are zone dependent. Thus, the echelettes 130 in zone 1 122 have a first radius of curvature, a first height and a first period. The echelettes 130 in Zone 2 124 have a second radius of curvature, a second height and a second period. In some embodiments, the zones 122, 124, 126 and 128 are configured such that zones closer to the optic axis 106 are for near vision while zones closer to the edge are configured for far vision. Thus, zones closer to the optic axis 106 have shorter focal length(s), while zone(s) closer to the edge have longer focal length(s). For example, the echelettes 130 for zone 1 122 may have a radius of curvature and periodicity that results in a shorter focal length than the echelettes 130 for zone 2 124. Similarly, the distance range for zone 1 122 may be set such that the focal length is shorter than for zone 2 124. Alternatively, the zones 122, 124, 126 and 128 may be configured so that the light transmitted through different zones 122, 124, 126 and 128 interferes in a manner that results in multiple focal lengths for the lens 110. In either case, each of the zones 122, 124, 126 and 128 may be considered to be associated with one or more focal lengths for the multifocal lens 110.

In a conventional lens, the height of the echelettes may be decreased for zones further from the optic axis. However, features of at least one zone closer to the optic axis 106 are repeated in at least one zone further from the optic axis in the lens 110. The height and/or radius of curvature for the echelettes 130 of a zone closer to the optic axis 106 are repeated for a zone further from the optic axis. In some embodiments, the period of the grating may also be repeated. For example, in the embodiment shown, the height and radius of curvature for the echelettes 130 of zone 1 122 are repeated in zone 3 126. Similarly, the height and radius of curvature for the echelettes 130 of zone 2 124 are repeated in zone 4 128. In alternate embodiments, only the height or only the radius of curvature of the echelettes 130 for an interior zone are repeated in a zone further from the optic axis 106.

The zones 122, 124, 126 and 128 may be repeated in various patterns. For example, the diffraction grating 120 might have zone 1 122, zone 2 124, repeated zone 1 (in zone 3 126) and repeated zone 2 (in zone 4 128). In such an embodiment, the echelettes 130 in zone 3 126 and zone 4 128 have the same height and/or radius of curvature as the echelettes 130 in zone 1 122 and zone 2 124, respectively. Such an embodiment is shown in FIGS. 1-2. In other embodiments, the zones may be zone 1 122, zone 2 124, zone 3 126 and repeated zone 1 (in zone 4 128). In such an embodiment, the echelettes 130 in zone 4 128 have the same height and/or radius of curvature as the echelettes of zone 1 122. The repetitions need not start with the zone closest to the optic axis 106. For example, the zones may be zone 1 122, zone 2 124, zone 3 126 and repeated zone 2 (in zone 4 128). In such an embodiment, the echelettes 130 in zone 4 128 have the same height and/or radius of curvature as the echelettes of zone 2 124. The repetitions need not continue throughout the diffraction grating 120. For example, the zones may be zone 1 122, zone 2 124, repeated zone 1 (in zone 3 126) and zone 4 128. In this embodiment, the echelettes 130 in zone 3 126 have the same height and/or radius of curvature as the echelettes of zone 1 122. However, the echelettes in zone 4 128 may have a different radius of curvature and step height than in any of the other zones 122, 124, 126 and 128. For lenses having more zones, the number of zones repeated may increase. For example, a lens (not shown) having seven zones may be configured (in order of increasing distance from the optic axis) zone 1, zone 2, zone 3, zone 4, repeated zone 1 (in zone 5), repeated zone 2 (in zone 6), and repeated zone 3 (in zone 7). In these various configurations, features of the echelettes in zone(s) further from the optic axis 106 have characteristics that are the same as those of the echelettes 130 in zone(s) closer to the optic axis.

The lens 110 and thus the ophthalmic device 100 may have improved adaptability to various patients. As discussed above, the height and/or radius of curvature of echelettes 130 in zone(s) further from the center of the lens 110 may be the same as the height and/or radius of curvature of echelettes 130 zone(s) closer to the center of the lens 110. Lenses may be designed such that one or more zones closer to the optic axis are configured for near vision, while zone(s) further from the optic axis are configured for far vision. In other words, a higher fraction of light transmitted by zones closer to the optic axis is used for near vision. A higher fraction of light transmitted by zones further from the optic axis may be dedicated to far vision. Repeating the characteristics of the inner zone(s) in regions closer to the edge of the lens 110 allows for a larger area to be dedicated to near vision. Stated differently, a larger fraction of the light energy passing through the lens 110 may be used for near vision. For individuals with larger pupil sizes, more light energy reaching the pupil is dedicated to near vision. This translates to improved near vision for such individuals. Thus, the zones 122, 124, 126 and 128 may be configured not only for correction of issues such as nearsightedness and presbyopia, but also to account for variations in the physical structure of patients' eyes, such as different pupil sizes. As such, various embodiments of the lens 110 and ophthalmic device 100 may be used for a variety of patients having various pupil sizes.

Figure 3:
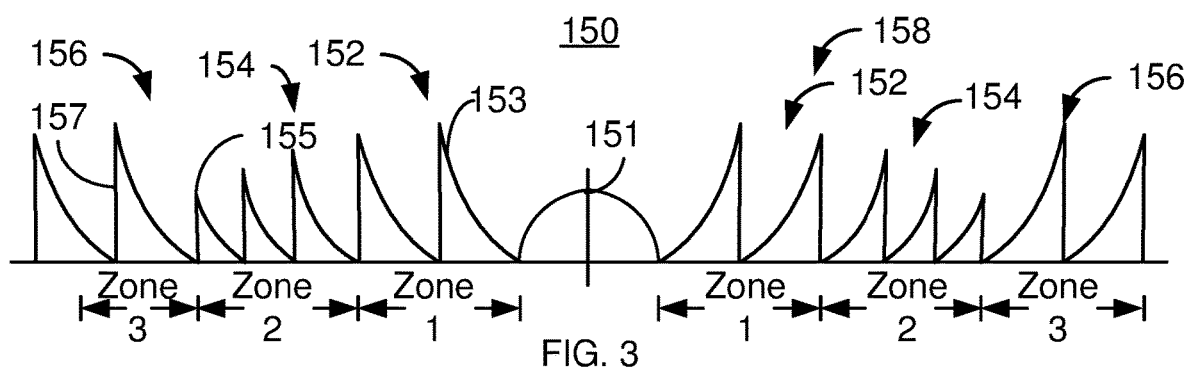
FIG. 3 is a side view depicting another exemplary embodiment of a diffractive grating for an exemplary embodiment of a portion of an ophthalmic device.
Figure 4:
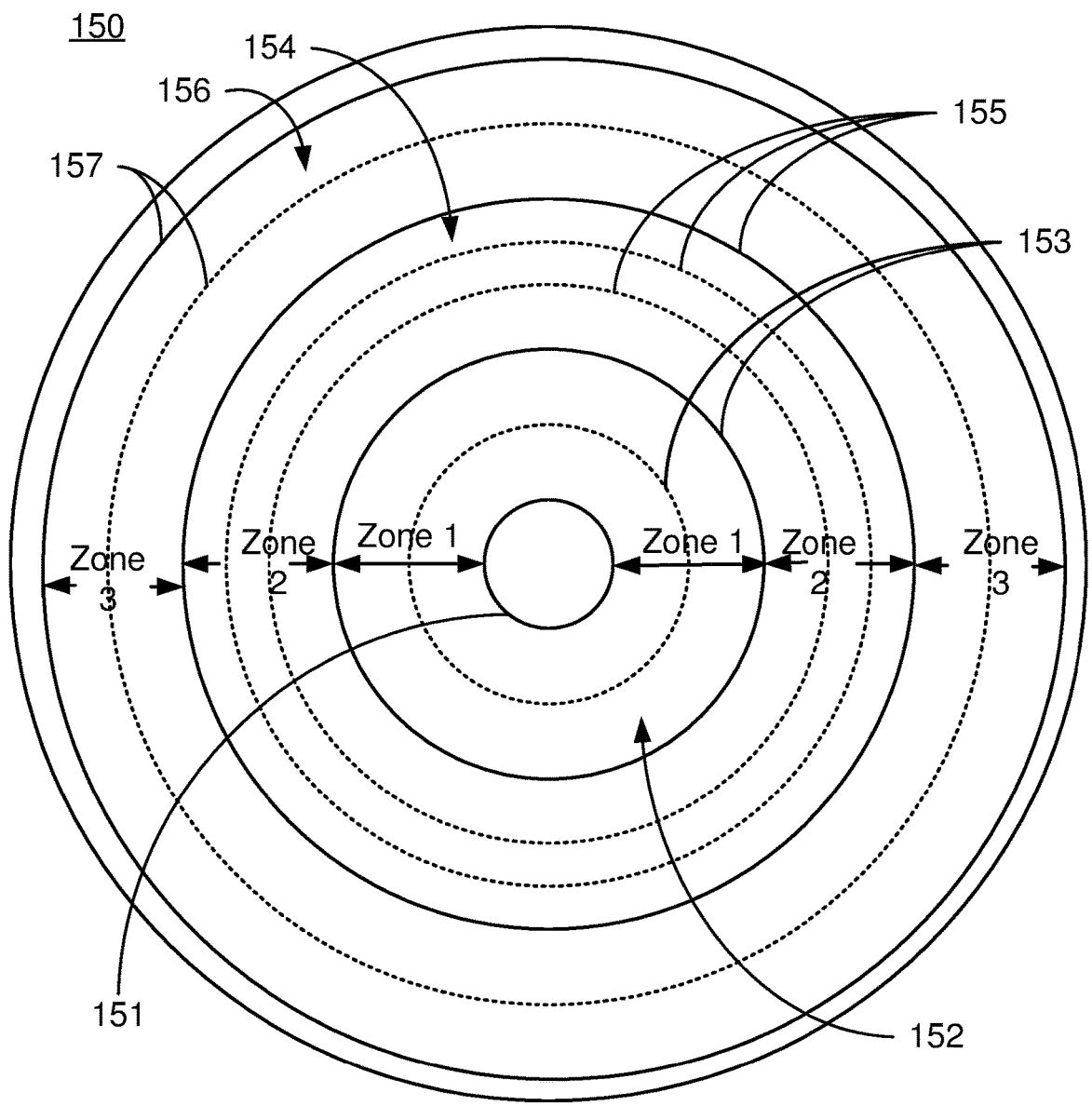
FIG. 4 depicts a plan view of exemplary embodiment of a lens for another exemplary embodiment of a portion of an ophthalmic device.

FIGS. 3 and 4 depict side and plan views of another exemplary embodiment of a lens 150. FIGS. 3 and 4 are not to scale. FIG. 3 depicts the height of the echelettes for the diffraction grating after the base curve has been removed. Consequently the view shown in FIG. 3 has a horizontal axis. However, the anterior and/or posterior surface on which the diffraction grating resides is typically curved. The lens 150 is analogous to the lens 110 and thus may be incorporated into the ophthalmic device 100. The lens 150 includes an optic axis, refractive element 151 and zones 152, 154 and 156 that form a diffraction grating 158. The zones 152, 154 and 156 include echelettes 153, 155 and 157, respectively. The refractive element 151, diffraction grating 158 and zones 152, 154 and 156 are analogous to the refractive element 118, diffraction grating 120 and zones 122, 124, 126 and 128, respectively. For clarity, only three zones 152, 154 and 156 are shown. However, another number of zones may be present. The zones 152, 154 and 156 may have different focal lengths, different echelette heights and/or different echelette radii of curvature. In at least some embodiments, zone 1 152 corresponds to shorter focal length(s) for near vision, while zone 2 154 corresponds to longer focal length(s) for distance vision. Thus, a zone closer to the optic axis is configured for near vision while a zone closer to the edge of the lens 150 is configured for distance vision.

In the embodiment shown the heights of the echelettes 153, 155 and 157 vary within the zones 152, 154 and 156, respectively. In each zone 152, 154 and 156, the heights of the echelettes 153, 155 and 157, respectively, decrease with increasing distance from the optic axis. However, zone 3 156 is a repeat zone for zone 1 152. Thus, the heights of the echelettes 157 are the same as those for the echelettes 153. In the embodiment shown, the echelettes 157 also have the same radius of curvature as the echelettes 153.

The lens 150 having the diffraction grating 158 shares the benefits of the lens 110 and ophthalmic device 100. Repeating the heights and/or radii of curvature of the echelettes of one or more zones further from the center of the lens 110 allows for a larger amount of the light energy to be dedicated to near vision. For individuals with larger pupil sizes, more light energy reaching the pupil may be dedicated to near vision. Near vision for such individuals may be improved. As such, various embodiments of the lens 150 may be used for a variety of patients having various pupil sizes.

Figure 5:
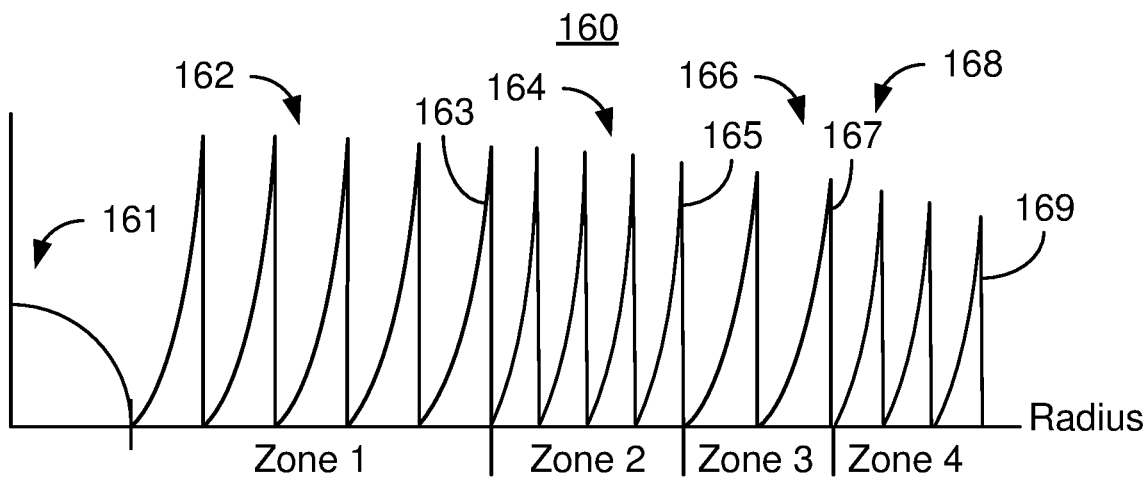
FIG. 5 is a side view depicting another exemplary embodiment of a diffractive grating for an exemplary embodiment of a portion of an ophthalmic device.

FIG. 5 depicts a side view of another exemplary embodiment of a diffraction grating 160 for a lens such as the lens 110 and/or 150. FIG. 5 is not to scale. FIG. 5 depicts the height of the echelettes for the diffraction grating after the base curve has been removed. Consequently the view shown in FIG. 5 has a horizontal axis. However, the anterior and/or posterior surface on which the diffraction grating resides is typically curved. The diffraction grating 160 is analogous to the diffraction grating(s) 120 and/or 158 and thus may be incorporated into the ophthalmic device 100. The lens includes an optic axis (at zero radius), refractive element 161 and zones 162, 164, 166 and 168 that form the diffraction grating 160. The zones 162, 164, 166 and 168 include echelettes 163, 165, 167 and 169, respectively. The refractive element 161, diffraction grating 160 and zones 162, 164, 166 and 168 are analogous to the refractive element 118, diffraction grating 120/158 and zones 122/152, 124/154, 126/156 and 128, respectively. For clarity, only four zones 162, 164, 166 and 168 are shown. However, another number of zones may be present. The zones 162, 164, 166 and 168 may correspond to multiple focal lengths and may have different distance ranges from the optic axis, different echelette heights and different echelette radii of curvature. In at least some embodiments, zone 1 162 has shorter focal length(s) for near vision, while zone 2 164 has longer focal length(s) for distance vision.

In each zone 162, 164, 166 and 168, the heights of the echelettes 163, 165, 167 and 169, respectively, decrease with increasing distance from the optic axis. In addition, the heights of the echelettes 163, 165, 167 and 169 monotonically decrease. However, zone 3 166 is a repeat zone for zone 1 162. Zone 4 is a repeat of zone 2 164. In the embodiment shown, only the radius of curvature repeats. Thus, the radii of curvature of the echelettes 167 are the same as those for the echelettes 163. In the embodiment shown, the echelettes 169 also have the same radius of curvature as the echelettes 165. Thus, two zones are repeated in the diffraction grating 160.

The lens including the diffraction grating 160 shares the benefits of the lenses 110/150 and ophthalmic device 100. Repeating the radii of curvature of the echelettes of one or more zones further from the center of the diffraction grating 160 may allow for a larger amount of the light energy to be dedicated to near vision. For individuals with larger pupil sizes, more light energy reaching the pupil may be dedicated to near vision. Near vision for such individuals may be improved. As such, various embodiments of the lens having the diffraction grating 160 may be used for a variety of patients having various pupil sizes.

Figure 6:
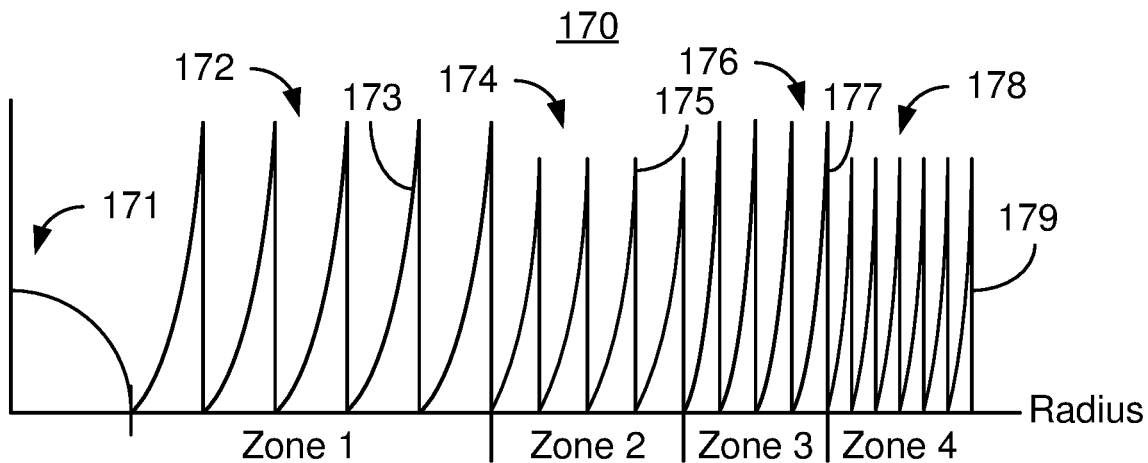
FIG. 6 is a side view depicting another exemplary embodiment of a diffractive grating for an exemplary embodiment of a portion of an ophthalmic device.

FIG. 6 depicts a side view of another exemplary embodiment of a diffraction grating 170 for a lens such as the lens 110 and/or 150. FIG. 6 is not to scale. FIG. 6 depicts the height of the echelettes for the diffraction grating after the base curve has been removed. Consequently the view shown in FIG. 6 has a horizontal axis. However, the anterior and/or posterior surface on which the diffraction grating resides is typically curved. The diffraction grating 170 is analogous to the diffraction grating(s) 120, 158 and/or 160 and thus may be incorporated into the ophthalmic device 100. The lens includes an optic axis (at zero radius), refractive element 171 and zones 172, 174, 176 and 178 that form the diffraction grating 170. The zones 172, 174, 176 and 178 include echelettes 173, 175, 177 and 179, respectively. The refractive element 171, diffraction grating 170 and zones 172, 174, 176 and 178 are analogous to similar elements depicted in FIGS. 1-5. For clarity, only four zones 172, 174, 176 and 178 are shown. However, another number of zones may be present. The zones 172, 174, 176 and 178 may correspond to multiple focal lengths and may have different distance ranges from the optic axis, different echelette heights and different echelette radii of curvature. In at least some embodiments, zone 1 172 has shorter focal length(s) for near vision, while zone 2 174 has longer focal length(s) for distance vision.

In each zone 172, 174, 176 and 178, the heights of the echelettes 173, 175, 177 and 179, respectively, are constant. However, between zones, the heights of the echelettes 173, 175, 177 and 179 decrease with increasing distance from the optic axis. Thus, the height of the echelettes 175 is less than the height of the echelettes 173. However, zone 3 176 is a repeat zone for zone 1 172. Zone 4 178 is a repeat of zone 2 174. In the embodiment shown, only the height repeats. Thus, the radius of curvature of the echelettes 177 differs from that of the echelettes 173. Similarly, the echelettes 179 have a different radius of curvature than the echelettes 175. Consequently, the period of the grating 170 also changes between zones 172, 174, 176 and 178.

The lens including the diffraction grating 170 shares the benefits of the lenses 110/150 and ophthalmic device 100. Repeating the heights of the echelettes of one or more zones further from the center for the diffraction grating 170 allows for a larger amount of the light energy to be dedicated to near vision. Stated differently, providing echelettes of greater height closer to the edge of the diffraction grating 170 may increase the fraction of light dedicated to near vision. For individuals with larger pupil sizes, more light energy reaching the pupil may be dedicated to near vision. Near vision for such individuals may be improved. As such, various embodiments of the lens including the grating 170 may be used for a variety of patients having various pupil sizes.

Figure 7:
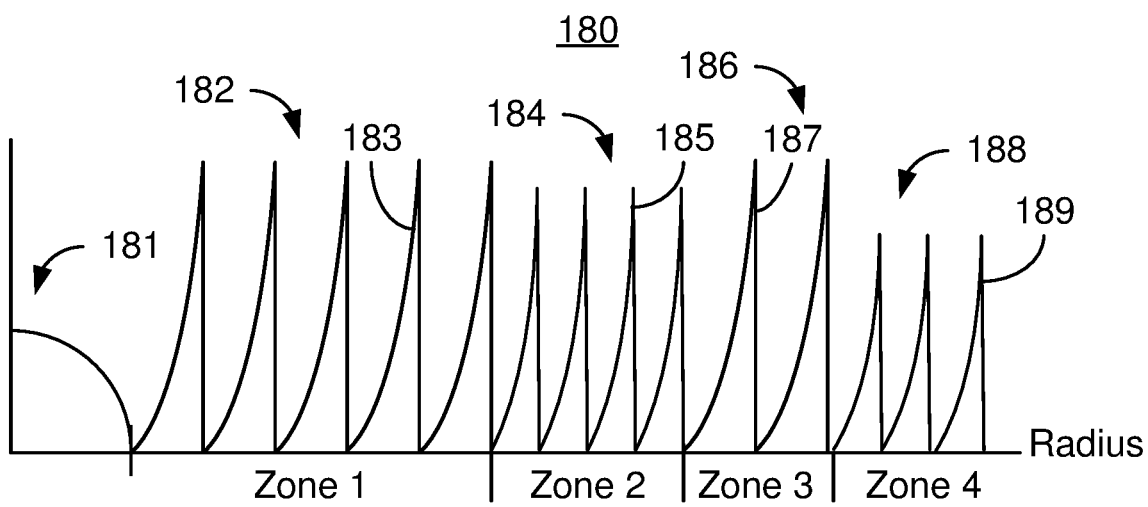
FIG. 7 is a side view depicting another exemplary embodiment of a diffractive grating for an exemplary embodiment of a portion of an ophthalmic device.

FIG. 7 depicts a side view of another exemplary embodiment of a diffraction grating 180 for a lens such as the lens 110 and/or 150. FIG. 7 is not to scale. FIG. 7 depicts the height of the echelettes for the diffraction grating after the base curve has been removed. Consequently the view shown in FIG. 7 has a horizontal axis. However, the anterior and/or posterior surface on which the diffraction grating 180 resides is typically curved. The diffraction grating 180 is analogous to the diffraction grating(s) 120, 158, 160 and/or 170 and thus may be incorporated into the ophthalmic device 100. The lens includes an optic axis (at zero radius), refractive element 181 and zones 182, 184, 186 and 188 that form the diffraction grating 180. The zones 182, 184, 186 and 188 include echelettes 183, 185, 187 and 189, respectively. The refractive element 181, diffraction grating 180 and zones 182, 184, 186 and 188 are analogous to similar elements depicted in FIGS. 1-6. For clarity, only four zones 182, 184, 186 and 188 are shown. However, another number of zones may be present. The zones 182, 184, 186 and 188 may correspond to multiple focal lengths and have different distance ranges from the optic axis, different echelette heights and different echelette radii of curvature. In at least some embodiments, zone 1 182 has shorter focal length(s) for near vision, while zone 2 184 has longer focal length(s) for distance vision.

In each zone 182, 184, 186 and 188, the heights of the echelettes 183, 185, 187 and 189, respectively, are constant. However, between zones, the heights of the echelettes 183, 185, 187 and 189 decrease with increasing distance from the optic axis. Zone 3 186 is a repeat zone for zone 1 182. However, zone 4 188 is not a repeat of zone 2 184. In the embodiment shown, only the height repeats. Thus, the radius of curvature of the echelettes 187 differs from that of the echelettes 183. In other embodiments, the radius of curvature may be repeated in lieu of or in addition to the height. In the embodiment shown, the entire pattern of zones need not be repeated. Thus, the diffraction grating includes zone 1 182, zone 2 184, repeated zone 1 (in zone 3 186) and zone 4 188. The echelettes 189 in zone 4 188 thus do not share the height or radius of curvature with the echelettes 186 of zone 2 184.

A lens including the diffraction grating 180 shares the benefits of the lenses 110/150 and ophthalmic device 100. Repeating the heights of the echelettes of one or more zones further from the center for the diffraction grating 180 allows for a larger amount of the light energy to be dedicated to near vision. For individuals with larger pupil sizes, more light energy reaching the pupil may be dedicated to near vision. Near vision for such individuals may be improved. As such, various embodiments of the lens including the grating 180 may be used for a variety of patients having various pupil sizes.

Figure 8:
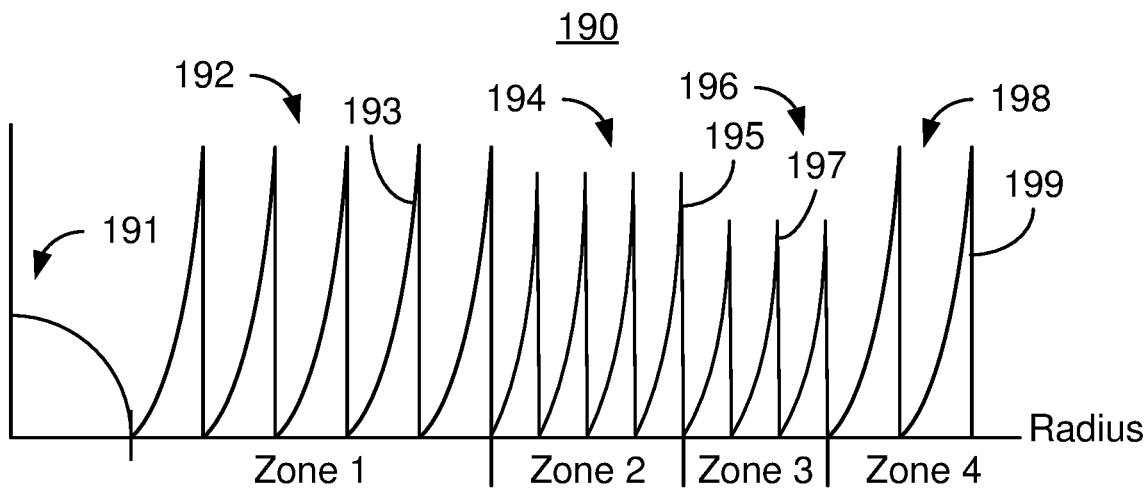
FIG. 8 is a side view depicting another exemplary embodiment of a diffractive grating for an exemplary embodiment of a portion of an ophthalmic device.

FIG. 8 depicts a side view of another exemplary embodiment of a diffraction grating 190 for a lens such as the lens 110 and/or 150. FIG. 8 is not to scale. FIG. 8 depicts the height of the echelettes for the diffraction grating after the base curve has been removed. Consequently the view shown in FIG. 8 has a horizontal axis. However, the anterior and/or posterior surface on which the diffraction grating 190 resides is typically curved. The diffraction grating 190 is analogous to the diffraction grating(s) 120, 158, 160, 170 and/or 180 and thus may be incorporated into the ophthalmic device 100. The lens includes an optic axis (at zero radius), refractive element 191 and zones 192, 194, 196 and 198 that form the diffraction grating 190. The zones 192, 194, 196 and 198 include echelettes 193, 195, 197 and 199, respectively. The refractive element 191, diffraction grating 190 and zones 192, 194, 196 and 198 are analogous to similar elements depicted in FIGS. 1-7. For clarity, only four zones 192, 194, 196 and 198 are shown. However, another number of zones may be present. The zones 192, 194, 196 and 198 may correspond to multiple focal lengths and may have different distance ranges from the optic axis, different echelette heights and different echelette radii of curvature. In at least some embodiments, zone 1 192 has more light dedicated to shorter focal length(s) for near vision, while zone 2 194 has more light dedicated to longer focal length(s) for distance vision.

In each zone 192, 194, 196 and 198, the heights of the echelettes 193, 195, 197 and 199, respectively, are constant. However, between zones, the heights of the echelettes 193, 195, 197 and 199 decrease with increasing distance from the optic axis. Zone 1 192, zone 2 194 and zone 3 196 progress in an expected manner. Zone 4 198 is a repeat zone for zone 1 192. In the embodiment shown, only the height repeats. Thus, the radius of curvature of the echelettes 199 differs from that of the echelettes 193. In other embodiments, the radius of curvature may be repeated in lieu of or in addition to the height. In the embodiment shown, the entire pattern of zones need not be repeated. Thus, the diffraction grating includes zone 1 192, zone 2 194, zone 3 196 and repeated zone 1 (in zone 4 198). Consequently, more than one zone (zones 194 and 196) are between the original zone 1 192 and the repeated zone 1 in zone 4 198.

A lens including the diffraction grating 190 shares the benefits of the lenses 110/150 and ophthalmic device 100. Repeating the heights of the echelettes of one or more zones further from the center for the diffraction grating 190 allows for a larger amount of the light energy to be dedicated to near vision. For individuals with larger pupil sizes, more light energy reaching the pupil may be dedicated to near vision. Near vision for such individuals may be improved. As such, various embodiments of the lens including the grating 190 may be used for a variety of patients having various pupil sizes.

Various features have been highlighted in the embodiments shown in FIGS. 1-8. One of ordinary skill in the art will readily recognize that these features may be combined and/or extended, for example to a larger number of zones, in a manner not inconsistent with the method and system described herein.

Figure 9:
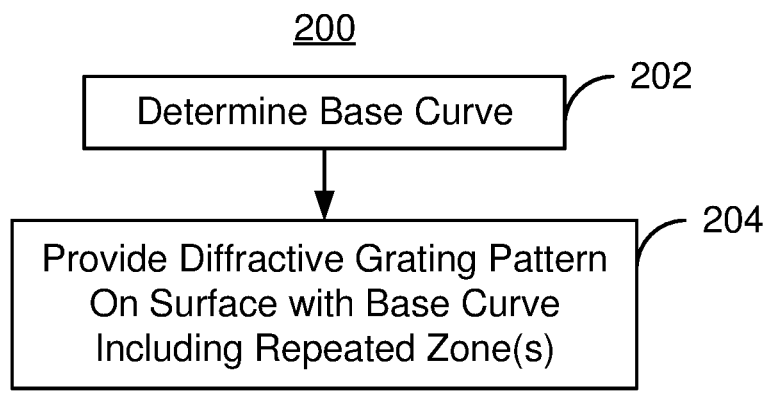
FIG. 9 is a flow chart depicting an exemplary embodiment of a method for providing an ophthalmic device.
Figure 10:
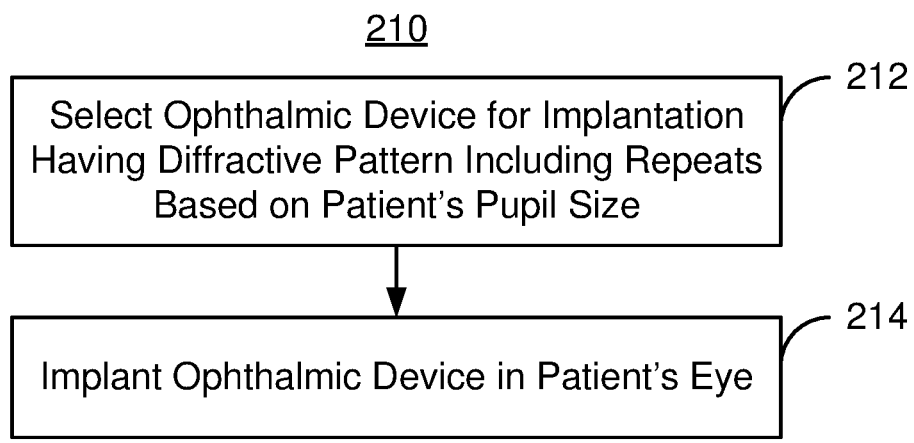
FIG. 10 is flow chart depicting an exemplary embodiment of a method for utilizing an ophthalmic device.

FIG. 9 is an exemplary embodiment of a method 200 for providing an ophthalmic lens. For simplicity, some steps may be omitted, interleaved, and/or combined. The method 200 is also described in the context of the ophthalmic device 100 and ophthalmic lens 110. However, the method 200 may be used with one or more of ophthalmic lenses 110 and 150 and diffraction gratings 120, 160, 170, 180 and/or 190 an analogous ophthalmic device.

Base curves for the anterior surface 114 and the posterior surface 112 of the ophthalmic lens 110 are determined, via step 202. Thus, the curvature of the surface(s) on which the diffraction grating 120 will reside and the curvature of the opposite surface (if any) are determined.

The diffraction grating(s) 120 are provided on the underlying base curve(s), via step 204. Thus, the shape a diffraction grating 120 having one or more repeated zones may be determined. This shape is also made part of the anterior and/or posterior surfaces as part of step 204. Thus, the shape of the lens 110 is determined and made.

Using the method 200, the ophthalmic lens(s) 110, 150 and/or ophthalmic lens may be provided. Thus, the benefits of one or more of the ophthalmic lenses 110 having diffraction grating(s) 120, 150, 22 may be provided and the benefits thereof achieved.

FIG. 9 is an exemplary embodiment of a method 210 for treating an ophthalmic condition in a patient. For simplicity, some steps may be omitted, interleaved, and/or combined. The method 210 is also described in the context of using the ophthalmic device 100 and ophthalmic lens 110. However, the method 210 may be used with one or more of ophthalmic lenses 110 and/or 150 including diffraction grating(s) 120, 150, 160, 170 180 and/or 190.

An ophthalmic device 100 for implantation in an eye of the patient is selected, via step 212. The ophthalmic device 100 includes an ophthalmic lens 110 having a diffraction grating 120. Thus, the ophthalmic device 100 including the grating 120, 160, 170, 180, and/or 190 may be selected in step 212. Part of the selection process may involve measuring the patient's pupil and having a lens with the appropriate zone(s) repeated in the desired location(s)

The ophthalmic device 100 is implanted in the patient's eye, via step 214. Step 214 may include replacing the patient's own lens with the ophthalmic device 100 or augmenting the patient's lens with the ophthalmic device. Treatment of the patient may then be completed. In some embodiments implantation in the patient's other eye of another analogous ophthalmic device may be carried out.

Using the method 210, the ophthalmic lens(s) having diffractive grating(s) on anterior and/or posterior surfaces and/or ophthalmic lens may be used. Thus, the benefits of one or more of the ophthalmic lenses 110 may be achieved.

A method and system for providing an ophthalmic lens having a diffraction grating, an ophthalmic device including the lens and a method for using the ophthalmic device have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. An ophthalmic lens comprising:
   an anterior surface;
   a posterior surface; and
   at least one diffraction grating including a plurality of zones corresponding to a plurality of radial distance ranges from a center of the ophthalmic lens, the plurality of zones including a first near vision zone corresponding to a first radial distance range from the center of the ophthalmic lens, a second distance vision zone corresponding to a second radial distance range, the second radial distance range further from the center of the ophthalmic lens than the first radial distance range, and a third near vision zone corresponding to a third radial distance range, the third radial distance range further from the center of the ophthalmic lens than the second radial distance range, wherein:

the first near vision zone includes a plurality of first echelettes each having a first step height and a first radius of curvature, the first echelettes configured to direct light transmitted by the plurality of first echelettes to a near vision focal point, the second distance vision zone includes a plurality of second echelettes each having a second step height and a second radius of curvature, the second step height being different than the first step height and the second radius of curvature being different than the first radius of curvature, the second echelettes configured to direct light transmitted by the plurality of second echelettes to a distance vision focal point, the third near vision zone includes a plurality of third echelettes each having the first step height and the first radius of curvature, the third echelettes configured to direct light transmitted by the plurality of third echelettes to the near vision focal point, such that a total fraction of light energy directed to the near vision focal point increases for pupils larger than a radially innermost boundary of the third near vision zone.

2. The ophthalmic lens of claim 1 wherein the anterior surface has a base curvature, the diffraction grating being disposed on the base curvature.

3. An ophthalmic device comprising:

an ophthalmic lens having an anterior surface, a posterior surface and at least one diffraction grating, the at least one diffraction grating including a plurality of zones corresponding to a plurality of radial distance ranges from a center of the ophthalmic lens, the plurality of zones including a first zone corresponding to a first radial distance range from the center of the ophthalmic lens, a second zone corresponding to a second radial distance range further from the center of the ophthalmic lens than the first distance range, and a third zone corresponding to a third radial distance range further from the center of the ophthalmic lens than the second radial distance range, wherein:

the first zone includes a plurality of first echelettes each having a first step height and a first radius of curvature, the first echelettes configured to direct light transmitted by the plurality of first echelettes to a near vision focal point, the second zone includes a plurality of second echelettes each having a second step height and a second radius of curvature, the second step height being different than the first step height and the second radius of curvature being different than the first radius of curvature, the second echelettes configured to direct light transmitted by the plurality of second echelettes to a distance vision focal point, the third zone includes a plurality of third echelettes each having the first step height and the first radius of curvature, the third echelettes configured to direct light transmitted by the plurality of third echelettes to the near vision focal point such that a total fraction of light energy directed to the near vision focal point increases for pupils larger than a radially innermost boundary of the third near vision zone;

a plurality of haptics coupled with the ophthalmic lens.

4. A method for providing an ophthalmic lens comprising:

providing at least one diffraction grating disposed on a base curve of of a surface of the ophthalmic lens, the at least one diffraction grating including a plurality of zones corresponding to a plurality of radial distance ranges from a center of the ophthalmic lens, the plurality of zones including a first zone corresponding to a first radial distance range from the center of the ophthalmic lens, a second zone corresponding to a second radial distance range further from the center of the ophthalmic lens than the first radial distance range, and a third zone corresponding to a third radial distance range further from the center of the ophthalmic lens than the second distance range, wherein:

the first zone includes a plurality of first echelettes each having a first step height and a first radius of curvature, the first echelettes configured to direct light transmitted by the plurality of first echelettes to a near vision focal point, the second zone includes a plurality of second echelettes each having a second step height and a second radius of curvature, the second step height being different than the first step height and the second radius of curvature being different than the first radius of curvature, the second echelettes configured to direct light transmitted by the plurality of second echelettes to a distance vision focal point, the third zone includes a plurality of third echelettes each having the first step height and the first radius of curvature, the third echelettes configured to direct light transmitted by the plurality of third echelettes to the near vision focal point such that a total fraction of light energy directed to the near vision focal point increases for pupils larger than a radially innermost boundary of the third near vision zone.

5. A method for treating an ophthalmic condition in a patient having a pupil size, the method comprising:

selecting an ophthalmic device for implantation in an eye of the patient based on the pupil size, the ophthalmic device including an ophthalmic lens having an anterior surface, a posterior surface and at least one diffraction pattern, the at least one diffraction grating including a plurality of zones corresponding to a plurality of radial distance ranges from a center of the ophthalmic lens, the plurality of zones including a first zone corresponding to a first radial distance range from the center of the ophthalmic lens, a second zone corresponding to a second radial distance range further from the center of the ophthalmic lens than the first distance range, and a third zone corresponding to a third radial distance range further from the center of the ophthalmic lens than the second radial distance range, the third radial distance range corresponding to the pupil size, wherein:

the first zone includes a plurality of first echelettes each having a first step height and a first radius of curvature, the first echelettes configured to direct light transmitted by the plurality of first echelettes to a near vision focal point, the second zone includes a plurality of second echelettes each having a second step height and a second radius of curvature, the second step height being different than the first step height and the second radius of curvature being different than the first radius of curvature, the second echelettes configured to direct light transmitted by the plurality of second echelettes to a distance vision focal point, the third zone includes a plurality of third echelettes each having the first step height and the first radius of curvature, the third echelettes configured to direct light transmitted by the plurality of third echelettes to the near vision focal point such that a total fraction of light energy directed to the near vision focal point increases as the pupil size exceeds a radially innermost boundary of the third near vision zone; and implanting the ophthalmic device in the eye of the patient.

* * * * *